United States Patent
Kirchhofer et al.

(10) Patent No.: US 7,686,782 B2
(45) Date of Patent: Mar. 30, 2010

(54) MULTI-CHAMBER AMPOULE WITH BYPASS AND PISTON SEAL

(75) Inventors: Fritz Kirchhofer, Sumiswald (CH); Christoph Rindlisbacher, Boll (CH)

(73) Assignee: TecPharma Licensing AG, Burgdorf (CH)

( * ) Notice: Subject to any disclaimer, the term of this patent is extended or adjusted under 35 U.S.C. 154(b) by 426 days.

(21) Appl. No.: 11/669,440

(22) Filed: Jan. 31, 2007

(65) Prior Publication Data
US 2007/0167908 A1    Jul. 19, 2007

Related U.S. Application Data

(63) Continuation of application No. PCT/CH2005/000460, filed on Aug. 5, 2005.

(30) Foreign Application Priority Data
Aug. 6, 2004    (DE)    ............ 20 2004 012 367 U

(51) Int. Cl.
  *A61M 37/00*    (2006.01)
(52) U.S. Cl. ................................ 604/90; 604/89
(58) Field of Classification Search ............ 604/59, 604/82, 89, 91, 219, 218, 222, 229, 90
See application file for complete search history.

(56) References Cited

U.S. PATENT DOCUMENTS

| | | | | |
|---|---|---|---|---|
| 4,020,750 A | * | 5/1977 | Freimuth et al. | ............ 92/205 |
| 4,968,299 A | * | 11/1990 | Ahlstrand et al. | ............ 604/90 |
| 5,395,326 A | * | 3/1995 | Haber et al. | ............ 604/90 |
| 5,891,087 A | * | 4/1999 | Ohtani et al. | ............ 604/89 |

FOREIGN PATENT DOCUMENTS

| | | |
|---|---|---|
| EP | 0793973 | 9/1997 |
| EP | 0911046 | 4/1999 |

* cited by examiner

*Primary Examiner*—Nicholas D Lucchesi
*Assistant Examiner*—Brooke M Matney
(74) *Attorney, Agent, or Firm*—Dorsey & Whitney LLP; David E. Bruhn, Esq.

(57) ABSTRACT

A multi-chamber ampoule including a housing with a longitudinal axis, at least one bypass operably associated with the housing, at least one front and one rear piston both of which can engage with the housing in a sealing manner outside the vicinity of the bypass and both of which may be displaced along the longitudinal axis, wherein the rear piston includes at least one material which can project into the bypass when the rear piston is in the region of the bypass.

18 Claims, 2 Drawing Sheets

MULTI-CHAMBER AMPOULE WITH BYPASS AND PISTON SEAL

CROSS-REFERENCE TO RELATED APPLICATIONS

This application is a continuation of International Application No. PCT/CH2005/000460, filed on Aug. 5, 2005, which claims priority to German Application No. 20 2004 012 367.3, filed on Aug. 6, 2004, the contents of both of which are incorporated in their entirety herein by reference.

BACKGROUND

The present invention relates to devices for administering, injecting, delivering or dispensing a substance and to methods of making and using such devices. More particularly, it relates to ampoules or substance containers associated with such devices, and to a multi-chamber ampoule adapted to prevent leakage or an undesired escape or movement of a substance contained therein, e.g., a fluid product. More particularly, it relates to a multi-chamber ampoule with two pistons, wherein one of the pistons displays a material for sealing a bypass and/or can act as an absorptive seal.

Multi-chamber ampoules are known in the prior art. By such multi-chamber ampoules, e.g., two-chamber ampoules, fluid products consisting of several components are administered to a patient, which components are not mixed together until shortly before the administration. Generally, provided for this purpose are, in a first chamber, a fluid consisting of solvent and, in a second chamber, a product component in solid or fluid state. The solvent and the product component are mixed together in the ampoule by a mixing device and/or process. With the aid of the mixing device, the fluid product to be injected can be mixed shortly before an administration by an administration device through the displacement of a plug in such a manner that, via a supply channel, the solvent comes into contact with the product component and mixes together with the latter.

In some embodiments of two-chamber ampoules, the fluid product component is located between two pistons. For the mixing together, a force is exerted on a piston, which force is transferred to the other piston through the incompressibility of the fluid, so that both pistons and the product component are pushed in a discharge direction, until the piston pointing in the discharge direction has been completely displaced into a region of a bypass, which region is formed through the housing. Via the bypass, the fluid product component is now guided past the piston, so that this piston only moves again when the rear piston strikes the front piston. From now on, both pistons are moved in the discharge direction, so that the mixed product can be discharged.

However, the bypass in the housing still contains, with the discharge movement, fluid remnants of the fluid product component. If both pistons have passed the bypass, then remnants of the fluid product component run or leak out of the bypass, in a direction opposite to the discharge direction, and into a region behind the pistons. From this arises the problem that the mechanism provided for the mixing and discharging of the contents of the two- or multi-chamber ampoule becomes contaminated. For one thing, this is unhygienic, and, for another thing, the mechanism could become fouled or gummed up and no longer function in an normal manner.

SUMMARY

The present invention provides an ampoule that at least minimizes the chance of leakage and/or unwanted movement of a substance to be dispensed. In one embodiment, the ampoule is a two chamber or multi-chamber ampoule that prevents the undesired escape of the contents of the ampoule.

In the following, references to "at the front" or "distal" are intended to refer to the portion, side or end of the ampoule that is in the discharge direction or is generally near the discharge end of the ampoule or a device with which the ampoule is being used, and references to "at the rear" or "proximal" are intended to refer to the opposite portion, side or end of the ampoule.

In some embodiments, a multi-chamber ampoule in accordance with the present invention comprises a housing with a longitudinal axis, at least one bypass formed on the housing, at least two pistons, for example at least one front and one rear piston, which pistons, outside the region of the at least one bypass, can lie against the housing in a sealing manner and are displaceable along the longitudinal axis, wherein a material is located in at least one partial region of a circumferential side of at least one of the pistons, for example the rear piston, which material can penetrate into the bypass when the at least one piston, for example the rear piston, is located in the region of the at least one bypass.

In one embodiment, the present invention comprises a multi-chamber ampoule comprising a housing with a longitudinal axis, a bypass operably associated with the housing, a front piston and a rear piston both of which can engage with the housing in a sealing manner outside the vicinity of the bypass and both of which may be displaced along the longitudinal axis, wherein the rear piston includes a material which can occlude and/or block the bypass when the rear piston is in the region of the bypass.

As a general rule, in some embodiments, the housing displays an approximately ring-shaped or cylindrical cross section. The ring is circular, but can also have an oval or angular shape, in which case the pistons are to be shaped such that they rest against the inner side wall or walls of the ampoule in a sealing manner. In at least one partial region of the housing is a radially outwardly-extending protrusion, which forms the bypass. The bypass may be formed by a relieved region or indentation in the wall or walls of the housing and can be an integral component of the housing, so that the bypass is formed on the housing, in the housing, or through the housing. In one preferred embodiment, the inward-most surface of the bypass, i.e., that surface facing into the housing, is axially parallel with the wall or walls of the housing. The radial difference between the inner side of the housing and the bypass is compensated through oblique planes extending in the longitudinal direction. However, these oblique planes can also be curves or rounded areas in the housing.

In some embodiments, at the end of the housing pointing in the discharge direction, the housing is closed. The closing can be formed, for example, through a collar in which a septum is located, which can be pierced by a needle. At an end side of the housing opposite to the septum, the multi-chamber ampoule is open, so that, for example, the piston rod of a mixing and/or discharging device can penetrate into the housing and rest against the rear piston, which can also seal in the region of the bypass. Formed in the housing by the at least two pistons are at least two chambers, which contain solid or fluid product components. A first chamber is formed by the distal end wall of the ampoule, a first piston, which permits a material flow in the region of the bypass, and the housing. A second chamber is formed by the first piston, the second piston, and the housing. Any additional chamber is formed appropriately, e.g., by additional appropriately positioned pistons in any number.

In some embodiments, the pistons display a length, extending in the longitudinal direction, that is in each case shorter than the axial length of a least one corresponding bypass. Thus, the flowing of the fluid product component past the piston through the bypass is made possible. The rear piston may be referred to or thought of as a closing piston. The closing piston may, but need not, have a longer axial length than the bypass or bypasses contained in the housing. The at least one front piston, which is located between the distal end wall of the ampoule and the closing piston, may be referred to or thought of as a separating piston.

By the application to the closing piston of a force in the discharge direction, this force, due to the incompressibility of the fluid or solid component, is transferred to the next separating piston in the housing. If the closing piston is displaced, then the displacement is also transferred to the next separating piston, until the latter has traveled so far into a bypass that a material transport is possible through the bypass. The separating piston now no longer lies against the ampoule wall in a completely sealing manner. Via the bypass, upon a further displacement of the closing piston, the product contained in front of this piston can flow past the separating piston located in the region of the bypass and mix with the product component located in the next chamber. When the closing piston strikes against the separating piston located next in the discharge direction, the entire product component has been displaced from the chamber formed earlier through the two pistons. In the case of a two-chamber ampoule, the mixing process would now be completed. In the case of a multi-chamber ampoule, at least one more mixing process of a possible sequence of mixing processes can take place, which process functions in like manner as just described. In this case, an additional product component is located between two separating pistons. The mixing process of the additional product component with another product component or a product mixture is completed when a proximal separating piston strikes against a distal separating piston. It is to be pointed out that in the mixing process of the multi-chamber ampoules the product components can be mixed together either approximately simultaneously or in sequence. The order of the sequential mixing process can be planned such that the product component located between a closing piston and a separating piston is mixed first. Thus, the product component located between two separating pistons would be mixed. However, other sequences are also possible.

In some embodiments, in a discharging process, the pistons, having been moved to lie against each other, are moved in the discharge direction, so that the previously-mixed product is discharged. At least one piston, in some preferred embodiments the closing piston, is designed such that, in the passing of the at least one bypass it prevents the escaping, movement or reflux of fluid remnants located in the bypass on the proximal side of the closing piston or ampoule. In some preferred embodiments, the closing piston prevents the reflux. Similarly, the bypass can also be sealed through, for example, one of the separating pistons.

In some embodiments, the material located in at least one partial region of a circumferential side of at least one piston, for example the rear piston, prevents fluid from flowing past the at least one piston via the bypass, for example past the rear piston. When the piston, e.g., the closing piston, passes the bypass, the material located on the circumferential side of the piston penetrates or expands into the bypass and seals the latter, and/or absorbs the fluid. Thus, an unwanted exiting or flow of the fluid in the direction of the open side of the ampoule is prevented. This is, for one thing, hygienic, and for another thing, protects the mechanism of a corresponding or complementary device used for or for powering or driving the mixing and discharging process.

In one embodiment, the at least one piston which prevents the reflux of the fluid remnants from the bypass or bypasses can consist of a first material forming the generally cylindrical body of the piston, the piston being at least partially covered with a second material that prevents the reflux of fluid remnants. In some embodiments, the piston can be formed of a single material, for example, a compressible material.

In one preferred embodiment, the second material extends in a ring-like manner around the rear piston or is arranged in a ring-like manner around at least part of the circumferential side of the piston. Further, the material can cover a portion of the piston or the entire circumferential side. Likewise, several rings of the second material can be arranged on the circumferential side.

In addition, in some embodiments, on the circumferential side or surface of at least one piston, e.g., the rear piston, at least one recess is formed. The above-described material can be located in the at least one recess or on the ridges or edges formed by the at least one recess. The at least one recess can be a circular groove or indent on the circumferential side of the piston, for example the rear piston, in which groove the material or rather rings formed of the material are located. In some preferred embodiments, the material is inserted prior to the assembly of the at least one piston displaying the recess, for example the rear piston. The rings can then have a cross section corresponding to the contour of the groove.

According to another embodiment, the piston can consist completely of a material that prevents the reflux of the fluid remnants. In particular, in this case a sealing material may be used, which material is elastically compressible such that it enters the bypass and occludes the latter when the piston is pushed into the region of the bypass.

In some embodiments, the piston can also be formed in a two-part or multiple-part manner. In particular, a combination of structures and/or materials, which are arranged in the axial direction one behind another, may be advantageous. Thus, for example a front or distal part of the piston can consist or be comprised of one material and the rear or proximal part of another material. In some embodiments, the piston, e.g., the rear piston, can consist of at least two different materials that are arranged serially along the longitudinal axis of the piston and/or the housing. According to the intended use or contents to be dispensed, the characteristics of the material can be sealing, swelling, fluid absorbing, elastically compressible, or a combination of these characteristics. In general, the material in the region outside of the bypass can be pre-stressed and/or can enter the bypass in an elastic manner. The material of the piston arranged in the distal direction can separate the material arranged in the proximal direction from a fluid product component, since the material is fluid-impervious and forms the fluid seal with the inner wall of the housing. If the material that prevents the reflux of the fluid product is, for example, absorbent, then through this embodiment form a soaking of this, for example, absorbent material with the fluid product already prior to the use of the ampoule is prevented.

In one preferred embodiment, the material that prevents the reflux of fluid remnants from the bypass is compressible, so that it can expand in the region of bypass. For this purpose, in addition to rubber-like materials, foams, foam-like materials, swelling and/or fluid-absorbing materials may be suitable.

In a further embodiment, the contour of the circumferential-side recess of the piston can be unequal to the cross section of the material. It is possible to imagine a contour of the recess that makes it possible for the material to disappear nearly completely into the recess when the material is located in the region outside the bypass. In that state, the housing presses the material into the recess. When the material reaches the bypass, the material, due its elasticity, emerges from the recess and enters the bypass. In some embodiments, the material is applied to the at least one piston, e.g., the rear piston, in a two-component injection molding process.

DETAILED DESCRIPTION

Figure 1:
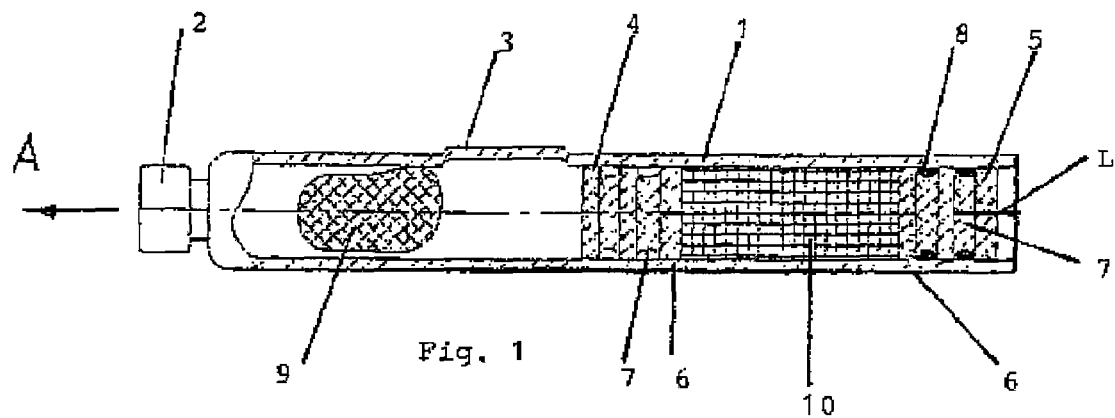
FIG. 1 shows a longitudinal section through one embodiment of a two-chamber ampoule in accordance with the present invention in an initial state.

FIG. 1 depicts a two-chamber ampoule in its initial state. The two-chamber ampoule comprises the housing 1 with a longitudinal axis L, through which housing a bypass 3 is formed. A collar 2 is carried or attached at the end of the housing 1 generally at the discharge end (the end pointing in the discharge direction A) of the housing. A septum that serves as the closure 2 of the two-chamber ampoule is located in the collar. The housing contains two pistons 4, 5, of which one piston is a closing piston 5 and the other is a separating piston 4. A front chamber is formed by the end of the housing, the separating piston 4 and the housing 3, and a product component 9 is located in the front chamber. The product component 9 is, in this case, a solid powder 9. A second chamber is formed by the separating piston 4, the closing piston 5, and the housing 1. A fluid product component 10 is located in the second, rear, chamber, and serves as a solvent for the product component 9 in the front chamber. Both pistons 4, 5 are arranged in the housing 1 in such a manner that they are displaceable along the axis L.

The separating piston 4 displays on its circumferential side two radial grooves 7. These grooves 7 serve to reduce the friction between the separating piston 4 and the housing 1. In principle, the separating piston 4 could also be designed without radial grooves 7. In this exemplary embodiment with grooves, the grooves display a semicircular contour. However, any other advantageous contour could be used. In FIG. 1, the closing piston 5 and separating piston 4 have the same features, but this is not an absolute requirement for a functional application of the two-chamber ampoule.

Located in the recesses 7 of the closing piston 5 is, in each case, an O-ring 8. The O-ring 8 comprises an elastic and/or compressible material. In addition, this material is suitable for forming a seal with the inner side of the housing 1 and the bypass 3. On the other hand, the material can also be absorbent, so that it is suitable for absorbing fluids to a certain degree. As is shown in FIG. 1, the O-rings 8 are located in a compressed state in the recesses 7 of the closing piston 5. To ensure that the O-ring 8, during the initial state of the two-chamber ampoule, does not come into contact with the product component 10, at least a part of the circumferential side 6 of the closing piston 5 forms a seal with the housing 1.

Figure 2:
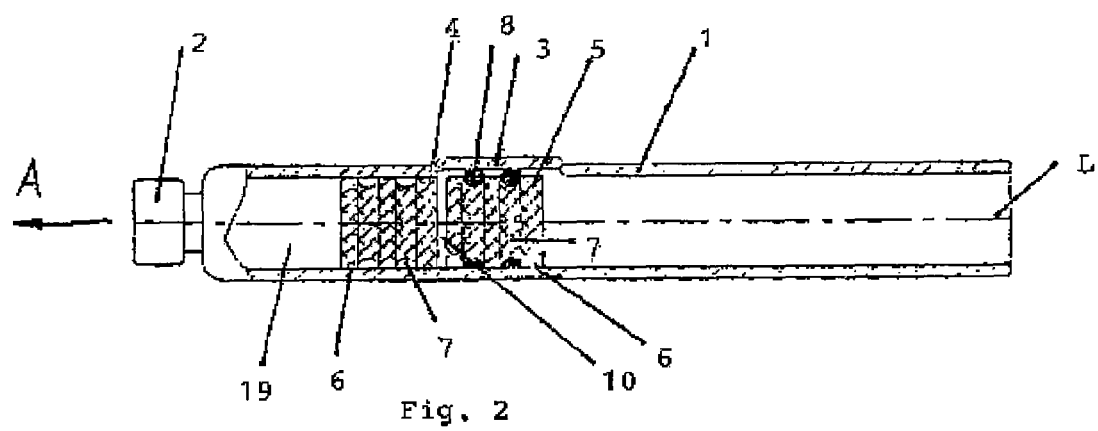
FIG. 2 shows a longitudinal section through a two-chamber ampoule according to FIG. 1, after the material has moved into the bypass.

FIG. 2 shows the two-chamber ampoule according to the present invention in a state in which the closing piston 5 is located with the O-rings 8 axially in the region of the bypass 3. Through the protrusion of the bypass 3, it is possible for the O-rings 8 to expand, by virtue of their elasticity, and to occlude and/or at least partially occupy the bypass 3. Through an appropriate selection of the material of the O-rings 8, a fluid seal is formed between the O-rings 8 and the bypass 3, which seal prevents the fluid remnants 10 from emerging from the bypass region into a region behind the closing piston 5, which region is opposite to the discharge direction A (i.e., generally at the end of the housing opposite the discharge end). In addition, the O-rings 8 can be formed of a material that is suitable for absorbing fluids. In this case, the fluid remnants 10 would be absorbed by the O-ring 8. Likewise, a combination of an absorbent material and a sealing material for the O-ring 8 is also conceivable. Since two O-rings are used in the closing piston 5, it can be advantageous to produce, for example, the O-ring 8 closest to the discharge end from a sealing material and the other O-ring 8 from an absorbent material. In this case, were the sealing O-ring 8 to not, in a normal manner, seal off the fluid remnants 10, then the other O-ring 8 could absorb the overflowing fluid remnants 10. An exiting of fluid remnants 10 from the bypass 3 is thus prevented.

Figure 3:
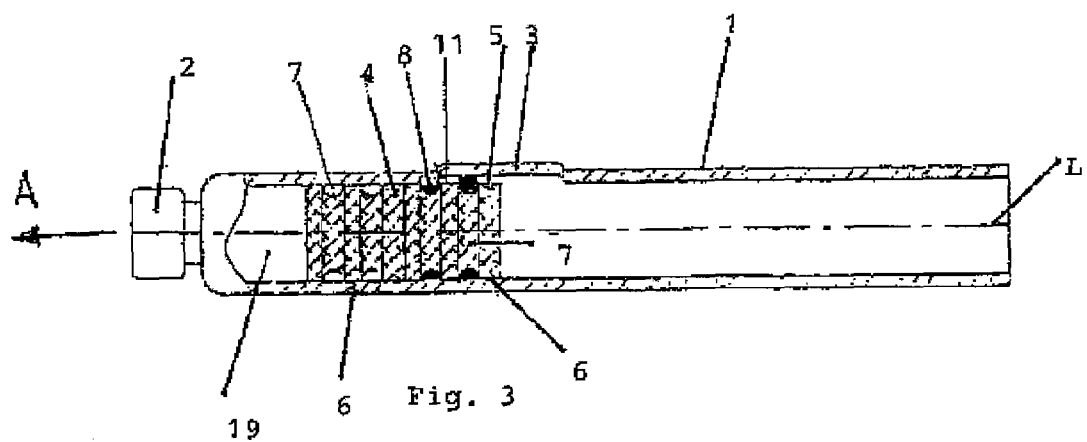
FIG. 3 shows a longitudinal section through a two-chamber ampoule according to FIG. 1, wherein the material has been pressed out of the bypass and back into the recesses.

FIG. 3 shows the moment in which the closing piston 5, together with the O-rings 8, leaves the axial region of the bypass 3. To be able to compensate the radial distance between the inner wall of the housing 1 and the bypass 3, ramp-like oblique bevels are formed as the transitions, which bevels, upon an axial movement of the closing piston 5 in the discharge direction, again press or rather compress the O-rings 8 into the grooves of the closing piston 5.

Figure 4:
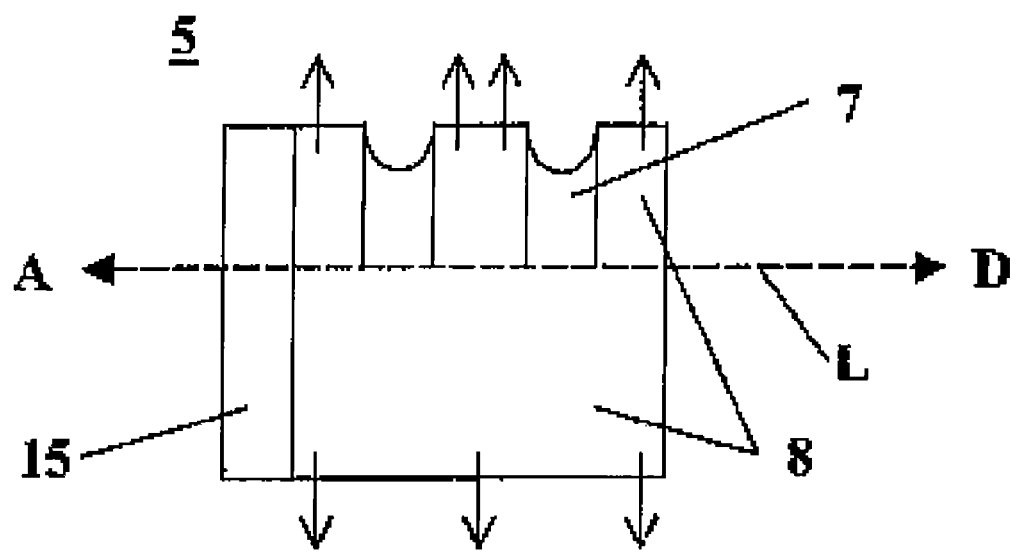
FIG. 4 shows a piston with two materials that are arranged serially in the axial direction.

FIG. 4 shows a piston, e.g., a closing piston 5, of a multi-chamber ampoule, which piston has a two-part form. The two parts 15, 8 are arranged serially or sequentially in the axial direction L, along the axis of the ampoule. The front part 15 of the piston 5 comprises a material that is fluid-impermeable, and forms a fluid seal with the inner wall of the housing 1. Through this, parts of the fluid component 10 that are located in the discharge direction A in front of the part 15 are prevented from moving past this part and reaching the expanding part 8, when the piston 5 is located outside the region of the bypass 3. The expanding part 8 of the piston 5 is formed such that, when it moves into the region of the bypass 3, it expands into and thus occludes the bypass 3. In addition, the expanding part 8 can consist of a material that, upon contact with the fluid component 10, begins to swell, i.e. absorb the fluid component. The portion of the expanding part 8 represented in FIG. 4 above the center line L displays, in contrast to the lower part, radially running or extending grooves 7, which reduce the contact surface of the expanding part 8 with the inner wall of the housing 1, so that frictional forces during the axial movement of the piston 5 are reduced.

Figure 5:
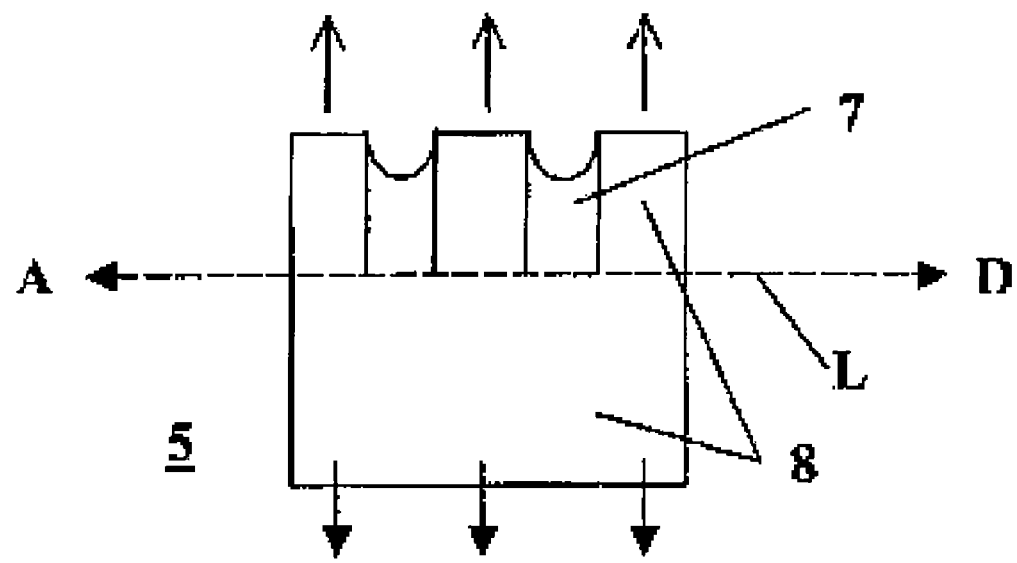
FIG. 5 shows a piston that is formed completely of one material.

FIG. 5 shows a piston 5 that is formed completely of one material, which material, when it is pushed into the region of the bypass 3, expands and occludes the bypass 3. Since the piston 5 is in constant contact with the product component 10, the piston 5 must be formed of a material that is not fluid-absorbent.

Suitable materials are those that, due to their elasticity, rest against the inner wall of the housing in a swelling or sealing manner and can penetrate, expand or extend into the bypass 3, to occlude or block the latter by occupying at least a portion of it.

In one embodiment, a sequence of use or function of an embodiment of a multichamber ampoule and administering device in accordance with the present invention comprises the following steps:

In the initial state (FIG. 1) of the two-chamber ampoule, the fluid solvent 10 is located between the closing piston 5 and the separating piston 4. The product component 9 to be dissolved is located between the separating piston 4 and the collar 2. Through application of a force to the closing piston 5, the latter is moved, during the mixing process, in the discharge direction A. In consequence of the incompressibility of the solvent 10, the movement is transferred to the separating piston 4, until the latter is axially located with its entire length in the region of the bypass 3. For this, in some embodiments, the separating piston 4 has a shorter axial length than the bypass 3. Since the solvent 10 now flows past the separating piston 4 via the bypass 3 to the front product component 9 and can thus mix with it, the separating piston 4 remains stationary until the closing piston 5 strikes against the separating piston 4. At this moment, the mixing process is completed. If the closing piston 5 is moved further in the discharge direction A, then it pushes the separating piston 4 likewise in this direction. This moment represents the beginning of the discharging process of the product mixture 9. Through the axial movement of the piston 5 in the discharge direction A, the closing piston 5 is moved axially into the region of the bypass 3. In the region of the bypass 3, the O-rings 8 are no longer compressed by the housing 1, so that, due to their elastic material, the O-rings 8 expand and move into the bypass 3. The O-rings 8 now prevent the reflux of fluid remnants 10 from the bypass 3 against the discharge direction, since the O-rings 8 form a sealing and/or fluid-absorbing element.

For completing the discharging of the product mixture 19, the closing piston 5 is further pressed in the discharge direction A, so that it leaves the region of the bypass 3 (FIG. 3). By means of the ram-like element 11, which acts as an oblique plane, the O-rings 8, through the axial movement of the closing piston 5, are radially compressed back into the recess 7 and are pre-stressed. The O-rings 8 are now located completely in the region of the housing 1, i.e. they are no longer in the region of the bypass 3. For completing the discharging of the product mixture 19, the closing piston 5 is pressed in the axial direction A until the forward side of the separating piston 4 abuts or lies against the discharge end of the housing 1.

Embodiments of the present invention, including preferred embodiments, have been presented for the purpose of illustration and description. They are not intended to be exhaustive or to limit the invention to the precise forms and steps disclosed. Obvious modifications or variations are possible in light of the above teachings. The embodiments were chosen and described to provide the best illustration of the principles of the invention and the practical application thereof, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A multi-chamber ampoule comprising:
 a housing with a longitudinal axis,
 a bypass structure associated with the housing,
 a front piston displaceable along the longitudinal axis, and
 a rear piston displaceable along the longitudinal axis and comprising an expandable material that contacts and expands at least partially into the bypass structure when the rear piston is located in the region of the bypass structure so as to seal the bypass structure.

2. The multi-chamber ampoule according to claim 1, wherein the rear piston comprises another material which sealingly contacts the housing.

3. The multi-chamber ampoule according to claim 1, wherein the expandable material is not fluid-absorbent.

4. The multi-chamber ampoule according to claim 3, wherein the rear piston is substantially of formed of the expandable material.

5. A multi-chamber ampoule comprising a housing with a longitudinal axis, a bypass operably associated with the housing, a first piston and a second piston, both pistons displaceable along the longitudinal axis and both engaging the housing in a sealing manner outside the vicinity of the bypass, wherein the second piston comprises a material which is elastically compressed as the material travels along the longitudinal axis outside the vicinity of the bypass, and when the second piston is in the region of the bypass, the compressed material expands into, blocks, and seals the bypass.

6. A multi-chamber ampoule comprising:
 a) a housing with a longitudinal axis,
 b) a bypass associated with the housing,
 c) a front piston and a rear piston, the rear piston displaceable along the longitudinal axis and, outside a region of the bypass, contacting the housing in a sealing manner, wherein
 d) the rear piston comprises a material that can enter the bypass when the rear piston is located in the region of the bypass
 e) wherein the material seals the bypass.

7. The multi-chamber ampoule according to claim 6, wherein the material prevents a fluid from flowing past the rear piston via the bypass.

8. The multi-chamber ampoule according to claim 6, wherein the material absorbs a fluid remaining in the bypass.

9. The multi-chamber ampoule according to claim 8, wherein the rear piston comprises a circumferential surface defining a circumferential recess.

10. The multi-chamber ampoule according to claim 9, wherein the material forms an o-ring arranged in the circumferential recess.

11. The multi-chamber ampoule according to claim 6, wherein the material that can enter the bypass is located in at least one partial region of a circumferential side of the rear piston.

12. The multi-chamber ampoule according to claim 11, wherein the material that can enter the bypass is inserted prior to the assembly of the multi-chamber ampoule.

13. The multi-chamber ampoule according to claim 12, wherein the material that can enter the bypass extends around the rear piston in a ring-like manner.

14. The multi-chamber ampoule according to claim 6, wherein the material that can enter the bypass is applied to the rear piston in a two-component injection molding process.

15. The multi-chamber ampoule according to claim 6, wherein the rear piston comprises at least two different materials, which are arranged serially along the longitudinal axis.

16. The multi-chamber ampoule according to claim 15, wherein one of the materials separates the other material from a fluid product component in the ampoule, the material separating the other material from the fluid product being fluid-impermeable and forms a fluid seal with the inner wall of the housing.

17. The multi-chamber ampoule according to claim 6, wherein the multi-chamber ampoule is a two-chamber ampoule.

18. The multi-chamber ampoule according to claim 6, wherein the material, at least in the region outside the bypass, is one of pre-stressed or can enter the bypass in an elastic manner.

* * * * *